US00PP17597P3

(12) United States Plant Patent
VanLaeken

(10) Patent No.: US PP17,597 P3
(45) Date of Patent: Apr. 17, 2007

(54) *CLEMATIS* PLANT NAMED 'CARNIVAL'

(50) Latin Name: ***Clematis* sp.**
Varietal Denomination: Carnival

(76) Inventor: James P. VanLaeken, 3242 Daansen Rd., P.O. Box 552, Walworth, NY (US) 14568

( * ) Notice: Subject to any disclaimer, the term of this patent is extended or adjusted under 35 U.S.C. 154(b) by 119 days.

(21) Appl. No.: 10/847,050

(22) Filed: May 17, 2004

(65) Prior Publication Data

US 2005/0257303 P1 Nov. 17, 2005

(51) Int. Cl.
*A01H 5/00* (2006.01)

(52) U.S. Cl. ..... Plt./228
(58) Field of Classification Search ..... Plt./228
See application file for complete search history.

(56) References Cited

U.S. PATENT DOCUMENTS

PP10,222 P * 2/1998 Evison ..... Plt./228
PP15,163 P2 * 9/2004 Olesen et al. ..... Plt./228
PP15,745 P2 * 5/2005 Olesen et al. ..... Plt./228

OTHER PUBLICATIONS http://www.prideofplaceplants.com/itm00061.htm.*
Spring Valley Greenhouse, Inc. Catalogue (4th ed).
Page 10 "General Sikorski".
Page 12 "Barbara Jackman".
Page 13 "Dr. Ruppert".

* cited by examiner

*Primary Examiner*—Wendy Haas
(74) *Attorney, Agent, or Firm*—Fred L. Denson

(57) ABSTRACT

A new variety of *clematis* plant named 'Carnival'. The variety is characterized by its unique color combination, having a medium lavender blue tepal with a dark lavender bar. The bright yellow stamens further distinguish the flowers.

1 Drawing Sheet

Botanical classification: *Clematis* sp.
Cultivar designation: 'Carnival'.

BACKGROUND OF THE NEW VARIETY

The present invention relates to a new and distinct variety of hybrid *clematis* plant known by the cultivar name 'Carnival'.

The new variety came from an individual seedling found growing in a controlled planting of cultivated plants in a *clematis* nursery in Walworth, N.Y. in 1999. Plants were asexually propagated and observed over the next two years. In 2002, an off-spring was selected and planted in an outside garden area and observed. Propagation was done in Walworth, N.Y. Asexual propagation by vegetative cuttings has shown that the propagules are identical to the original plant in all distinguishing characteristics. The stability of the variety is evidenced by the distinguishing characteristics remaining true to form from generation to generation. The parentage of the variety is unknown. However, it resulted from a chance seedling which was located in close proximity to *Clematis* sp. 'Barbara Jackman' and *Clematis* sp. 'General Sikorski'.

SUMMARY OF THE INVENTION

Among the features which distinguish the new variety from other presently available and known commercial *clematis* cultivars are the unique color of the flower. The flower has medium lavender blue tepals with a dark lavender bar that typically extends along its center longitudinal axis. The large bright yellow stamens further distinguish the flowers.

RELEVANT PRIOR ART

The new variety is somewhat similar in appearance to *Clematis* sp. 'Dr. Ruppel' variety as shown in the Spring Valley Greenhouse, Inc. catalogue ($4^{th}$ Edition) at page 13. While they both have slightly wavy edges, the 'Carnival' variety has a smaller flower and a striking blue color with a deeper purplish bar. They both have large showy stamens, however, 'Carnival' stamens are bright yellow whereas the *Clematis* sp. 'Dr. Ruppel' variety has a brown tinge to the tips.

BRIEF DESCRIPTION OF THE PHOTOGRAPH

The accompanying photograph illustrates the overall appearance of the new variety. The flowering and foliage colors as shown are, within the limitations of color photography, accurate and true reproductions of the actual colors of the new variety. The photographic view is a front elevation of typical *Clematis* sp. 'Carnival'.

BOTANICAL DESCRIPTION

The following information is based on a three year old plant grown in 50% shade in a 5 gallon container in a covered greenhouse with 60° F. ambient night temperatures and 75° F. ambient day temperatures in Walworth, N.Y. Color references are based on using the PANTONE® matching system.

I. Plant.

*A. Form.*—Upright climbing or spreading.

*B. Growth.*—Vigorous, vining. 1. Height: approximately 6 feet to 8 feet. 2. Diameter/Spread: approximately 2 feet to 3 feet.

*C. Foliage.*—Deciduous, compound-trifoliate, opposite. 1. Size, typical and observed: a. compound leaf length 2.5 inches, width 5 inches. b. individual leaflets length 2.25 inches, width ⅞ inch. c. leaflets per compound leaf: 3. 2. Quantity of leaves per stem: typical and observed about 45; 2 to 4 simple leaves on lower stem. 3. Color a. upper surface: dark green (PANTONE® #371C). b. lower surface: medium green (PANTONE® #377U). 4. Shape, typical and observed a. leaflets: base is rounded; apex is pointed; margin is untoothed with glabrous edge. b. simple leaves: base is heart-shaped; apex is pointed; margin is untoothed with glabrous edge. 5. Texture, typical and observed a. upperside of simple and compound leaves: glabrous veined, b. underside of simple and compound leaves: ribbed. c. veination pattern for compound leaves: pinnate with green coloration on the upper and lower surfaces. d. veination pattern for simple leaves: palmatic with green coloration on the upper and lower surfaces. 6. Petiole a. color: (PANTONE® 497C). b. length, typical and observed. 1 inch. c. diameter, typical and observed: 3/64 inch.

*D. Wood.*— 1. New shoots a. color: light green (PANTONE® #575C). b. bark: smooth. c. internodes: cylindrical, approximately 3 inches in length and 1/16 inch in diameter. 2. Old Wood a. color: light brown (PANTONE® #175C). b. bark: smooth.

*E. Hardiness.*—US Zones 4 through 8. 1. low temperature tolerance, typical and observed: −10° F. to 0° F. 2. high temperature tolerance, typical and observed. 90° F. to 110° F.; requires 6 to 8 weeks dormancy at 35° F. to 40° F. to remain vigorous.

*F. Disease.*— 1. subject to any disease that normally affects *clematis* a. wilt. b. botrytis. 2. has shown resistance to powdery mildew.

*G. Pests.*—Subject to any pests that normally affect *clematis.*

II. Flower:

*A. Blooming habit.*—Recurrent, May, June and September based on climate in Rochester, N.Y. area.

*B. Bud.*— 1. Size: typical and observed from about ⅜ inch to about ¾ inch in length and about 3/16 inch to ⅜ inch diameter. 2. Form: elliptic to ovate. 3. Color: green/grayish white (PANTONE® #465C).

*C. Stem.*— 1. Dimensions, typical and observed: length approximately 6 feet to 8 feet; diameter between 1/16 and ⅛ inch. 2. Aspect: vertical. 3. Strength: erect. 4. Color: green (PANTONE® #378C).

*D. Bloom.*— 1. Size: typical and observed from about 3½ inches to about 6 inches in diameter with a depth of ½ inch. 2. Form: round, very symmetrical with 4, 5 or 6 tepals of equal size slightly overlapping. 3. Color upper surface: edges of tepals are lavender blue (PANTONE® #264C) with a darker bar (PANTONE® 248C). 4. Color lower surface: Outer edge same as upper surface (PANTONE® #264U); center bar is whitish with a hint of grey (PANTONE® #427C). 5. Characteristics: borne on 3 inch to 4½ inch stems. 6. Quantity: 1 bloom per stem; from 2 or 3 to several hundred blooms per plant depending on age and size of plant. 7. Lastingness: about 3 to about 6 days as a cut flower and about 7 to about 10 days on the plant.

*E. Tepals.*— 1. Form: obovate in shape starting 3/16 inch wide at base, expanding halfway up to 1⅛ inches at its widest point and then tapering down to a pointed apex, the typical and observed tepal base being wedge shaped and the overall tepal length being about 2 to 3 inches. 2. Arrangement: regularly arranged, slight overlapping at the base. 3. Fragrance: none. 4. Color: (see II D 3 and II D 4 above).

III. Reproductive organs:

*A. Stamens, filaments and anthers.*— 1. Arrangement: regularly arranged. 2. Stamens: typical and observed, 65 to 70 per bloom, (PANTONE® #461C), length 9/16 inch. 3. Anther: (PANTONE® #463C), length 3/16 inch. 4. Pistil: typical and observed, from about 30 to 35 per bloom, ⅜ inch in length.

*B. Pollen.*— 1. Color: off white. 2. Amount: Scarce.

*C. Styles.*—Bunched, even, average length.

*D. Stigmas.*— 1. Color: greenish-white (PANTONE® #365C).

*E. Seed, typical and observed.*— 1. Diameter: ⅛ inch. 2. Thickness: 1/32 inch. 3. Color: (PANTONE® #463U). 4. Shape: round. 5. Quantity per bloom: 8 to 15. 6. Description: ¾ inch long persistent style which is clothed with 1/32 inch long silky hairs.

I claim:

1. A new and distinct variety of *clematis* plant named 'Carnival' as shown and described herein.

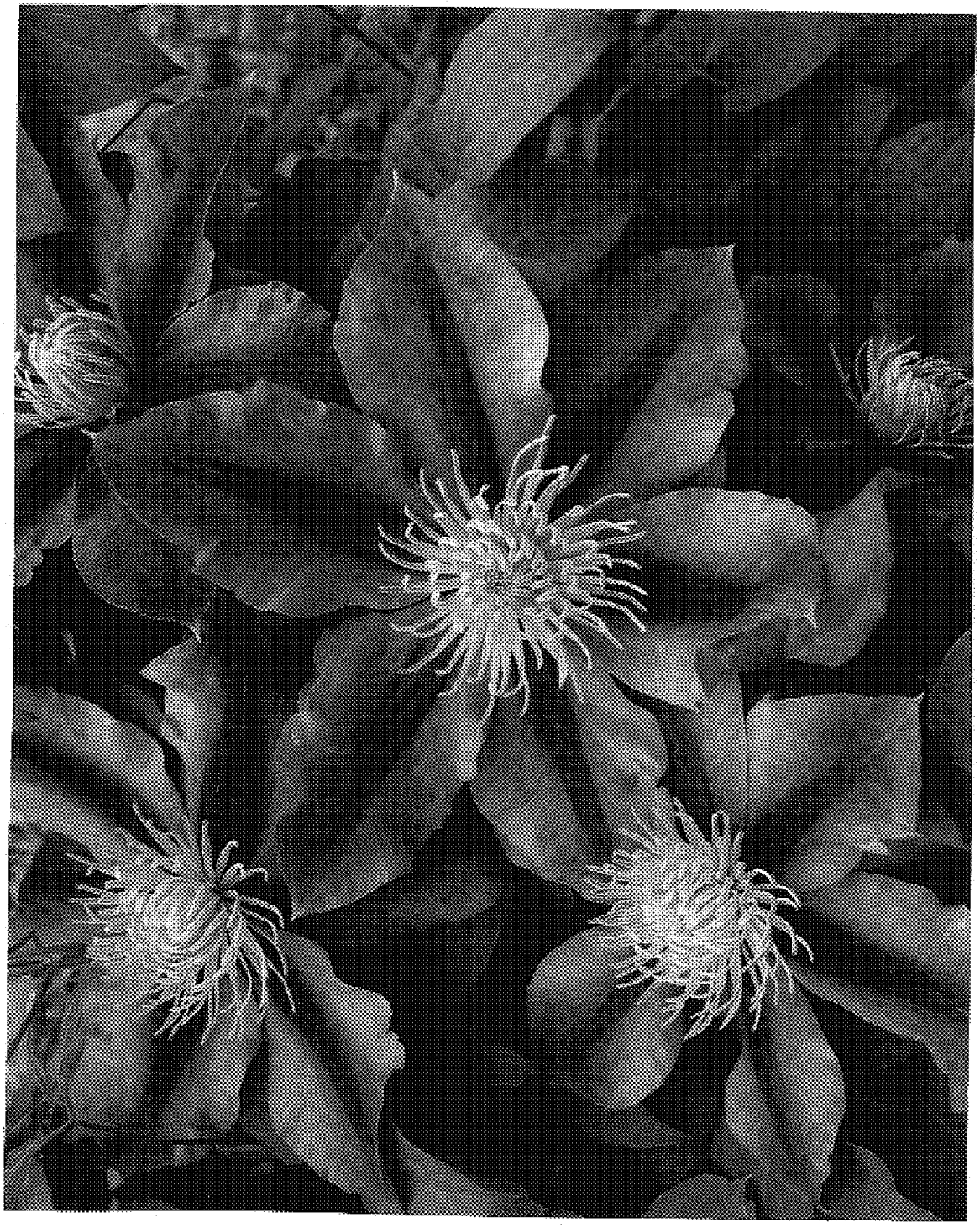

* * * * *